(12) United States Patent
Gerlach et al.

(10) Patent No.: US 7,108,856 B2
(45) Date of Patent: Sep. 19, 2006

(54) CD4+ T-LYMPHOCYTE-SPECIFIC HEPATITIS C VIRUS-EPITOPES

(75) Inventors: Jörn Tilman Gerlach, Munich (DE); Helmut Diepolder, Munich (DE)

(73) Assignee: Immusystems GmbH, Munich (DE)

( * ) Notice: Subject to any disclaimer, the term of this patent is extended or adjusted under 35 U.S.C. 154(b) by 0 days.

(21) Appl. No.: 10/397,411

(22) Filed: Mar. 26, 2003

(65) Prior Publication Data

US 2003/0186224 A1     Oct. 2, 2003

Related U.S. Application Data

(63) Continuation of application No. PCT/EP01/11263, filed on Sep. 28, 2001.

(30) Foreign Application Priority Data

Sep. 28, 2000   (EP)   ................... 00121138

(51) Int. Cl.
| | |
|---|---|
| A61K 39/00 | (2006.01) |
| A61K 39/12 | (2006.01) |
| A61K 39/29 | (2006.01) |
| A61K 38/00 | (2006.01) |
| A61K 38/03 | (2006.01) |
| C07K 4/00 | (2006.01) |
| C07K 4/02 | (2006.01) |
| C12Q 1/00 | (2006.01) |
| C12Q 1/18 | (2006.01) |
| G01N 33/53 | (2006.01) |

(52) U.S. Cl. ............... 424/228.1; 424/185.1; 424/186.1; 424/189.1; 424/204.1; 514/2; 530/300; 530/328; 435/5; 435/7.1

(58) Field of Classification Search ............... 530/300, 530/326, 327, 328; 424/184.1, 185.1, 186.1, 424/189.1, 204.1, 228.1; 455/5, 7.1; 514/2
See application file for complete search history.

(56) References Cited

U.S. PATENT DOCUMENTS 5,709,995 A     1/1998  Chisari et al.
2004/0091995 A1*  5/2004  Schlom et al. ........... 435/235.1

FOREIGN PATENT DOCUMENTS

| EP | WO 01/24822 | * | 4/2001 |
|---|---|---|---|
| JP | 7-285994 | | 10/1995 |
| WO | WO 93/06247 | | 4/1993 |
| WO | WO 94/13699 | | 6/1994 |
| WO | WO 94/20127 | | 9/1994 |
| WO | WO 95/22317 | | 8/1995 |
| WO | WO 98/32456 | | 7/1998 |
| WO | WO 99/02183 | | 1/1999 |
| WO | WO 99/45954 | | 9/1999 |
| WO | WO 99/58658 | | 11/1999 |

OTHER PUBLICATIONS

Rollier et al., Journal of Virology, vol. 78 No. 1, pp. 187-196 (Jan. 2004).*
Heile et al., Journal of Virology, vol. 74 No. 15, pp. 6885-6892 (Aug. 2000).*
Koziel et al., Journal of Virology, vol. 67 No. 12, pp. 7522-7532 (Dec. 1993).*
Lazdina et al., Journal of General Virology, vol. 82, pp. 1299-1308 (2001).*
Definitions of "medicament," "medicinal," and "vaccine", The On-line Medical Dictionary, cancerweb.ncl.ac.uk/omd/.*
Ruppert et al., Proceeding of the National Academy of Sciences, USA, vol. 90, pp. 2671-2675 (1993).*
Diepolder et al., Journal of Virology, vol. 75 No. 17, pp. 7803-7810 (2001).*
Deveraux et al., Journal of General Virology, vol. 78, pp. 583-590 (1997).*
Alexander et al., Human Immunology, vol. 59 No. 12, pp. 776-782 (Dec. 1998).*
Chang et al., Journal of Clinical Investigation, vol. 100 No. 9, pp. 2376-2385 (Nov. 1997).*
Choo et al., Proceeding of the National Academy of Sciences, vol. 88 No. 6, pp. 2451-2455 (Mar. 1991).*
Fan et al., APMIS, vol. 108 Nos. 7-8, pp. 531-538 (Jul.-Aug. 2000).*
Derwent Publications Ltd., London, GB, English language abstract of JP 7-285994, "Synthetic peptide(s) with high reactivity to serum from patient with hepatitis C virus—used for diagnosis of HCV infection." 1995.
Tanaka et al., 1992 Virus Research 23: 39-53.

* cited by examiner

*Primary Examiner*—James C. Housel
*Assistant Examiner*—Zachariah Lucas
(74) *Attorney, Agent, or Firm*—Foley & Lardner LLP (57) ABSTRACT

The invention relates to Hepatitis C virus epitopes which are specific in relation to CD4+ T lymphocytes, in addition to vaccinations which contain said epitopes.

1 Claim, 9 Drawing Sheets

FIGURE 1

FIGURE 2

Epitope mapping of CD4+ T-Cell clones

Epitope aa1585-1594

```
 1575           1585         1594            1604
  |              |            |               |
* QTKQSGENLPYLVAYQATVC
            * YLVAYQATVCARAQAPPPSW
       * NLPYLVAYQATVCAR
        * LPYLVAYQATVCAR
         * PYLVAYQATVCAR
          * YLVAYQATVCAR
             LVAYQATVCAR
              VAYQATVCAR
               AYQATVCAR
       * NLPYLVAYQATVCAR
       * NLPYLVAYQATVCA
       * NLPYLVAYQATVC
         NLPYLVAYQATV
         NLPYLVAYQAT
         NLPYLVAYQA
```

YLVAYQATVC Epitope
*stimulates specific T-cell clone

CD4+ T-LYMPHOCYTE-SPECIFIC HEPATITIS C VIRUS-EPITOPES

CROSS-REFERENCE TO RELATED APPLICATIONS

This application is a continuation of PCT/EP01/11263, filed Sep. 28, 2001 and EP00121138.2, filed Sep. 28, 2000, which is herein incorporated by reference in its entirety.

BACKGROUND OF THE INVENTION

The invention relates to Hepatitis C virus-epitopes, which are specific with respect to CD4+ T-lymphocytes, and to vaccines containing these epitopes.

The Hepatitis C virus, termed HCV in the following, was identified in 1989 and is an RNA virus from the family of flaviviridae. It consists of one single strand of RNA of approx. 9400 nucleotides which code a precursor polyprotein of about 3000 amino acids in length. This polyprotein is translated in an open reading frame and split post-translationally and proteolytically. The virus is highly variable and various virus isolates exist which are designated as genotypes and the geographical distribution of which varies largely. More than six genotypes throughout the world have now been differentiated. These genotypes are in turn subdivided into subtypes. The genetic variability is present inter-individually and intra-individually (within an infected individual). The intra-individual subtypes are the so-called HCV quasi-species which are related but different virus sequences occurring with imprecise replication.

With a prevalence of approx. one to three percent worldwide, Hepatitis C is one of the most important chronic virus infections. At least 180 million individuals are thought to be currently infected. According to calculations by the Center of Disease Control in the USA, due to the long latency period after infection with HCV, there will still be an increase in illness associated with Hepatitis C until the year 2010.

The HCV is primarily transmitted parenterally and, until it was discovered, it was the main cause of post-transfusion hepatitis NonA-NonB. Due to the testing of all blood products on a routine basis with HCV antibody tests of the 2nd and 3rd generation, the number of post-transfusion hepatitis cases has reduced drastically. The so-called sporadic Hepatitis C infections. Currently there are no known measures of effectively preventing new infections along these routes.

The HCV causes a chronic inflammation of the liver (hepatitis) which in the course of many years can lead to other complications such as liver cirrhosis. Within the framework of a liver cirrhosis lasting some years about 5% of all infected persons develop a hepatocellular carcinoma. Consequently, in the western world Hepatitis C takes the first place as the cause of liver transplantations. The costs for the public health service due to these transplantations are substantial.

Although with chronic Hepatitis C antibodies can be found against almost all virus proteins, in contrast to Hepatitis B however, there is no anti-HCV antibody constellation which indicates an immunity to HCV or a cure. Also the presence of antibodies against the HCV during a chronic HCV infection does not alleviate the course of the illness. On the contrary, a successful therapy appears to be linked to a reduction in the antibody titre. Therefore, it is not possible to prevent an infection with Hepatitis C through a conventional, prophylactic vaccination with envelope protein as is successfully carried out with Hepatitis B. A therapeutic vaccination is therefore currently not available.

The only currently approved therapy is a treatment with interferon-alpha alone or in combination with ribavirin for three to twelve months. This form of therapy is very cost-intensive, it often involves side effects and leads to a permanent elimination of the virus in only about 40% of cases.

From the Journal of Virology, Volume 71, pages 6011 to 6019 and Hepatology, Volume 30, No. 4, 1999, pages 1088 to 1098 it is known that through direct peripheral blood T-cell stimulation and specificity analysis of HCV-specific T-cell lines, highly immunogenous T-cell epitopes can be identified within the core and NS3 and NS4 regions of the Hepatitis C virus. Here, T-lymphocytes are isolated from peripheral blood and the CD4+ T-lymphocytes specific to HCV which it contains are enriched to so-called specific T-cell lines by repeated stimulation with the appropriate virus protein in vitro. Through the analysis of the growth behaviour (inclusion of radioactively labelled nucleotides) of these specific T-cell lines after stimulation with HCV protein and/or the smaller subunits, the peptides, the sequence of the T-cell epitope can be narrowed down. In particular the analysis of T-cell lines produces in comparison to T-cell clones inexact results with regard to the sequence specifically recognised by the CD4+ T-lymphocytes due to the cell mixture.

It is therefore the object of this invention to isolate HCV epitopes specific to CD4+ T-lymphocytes and to make available the HCV epitopes identified through the CD4+ T-lymphocytes for a vaccine for the prophylaxis and/or therapy of an HCV infection.

SUMMARY OF THE INVENTION

The solution of the object are the following quoted HCV epitopes specific to CD4+ T-lymphocytes containing the sequence:

1) YLVAYQATVC;
   (SEQ ID NO:1)

2) VVTSTWVLVGGVLAALAAYCL;
   (SEQ ID NO:2)

3) QYLAGLSTLPG;
   (SEQ ID NO:3)

4) IASLMAFTA;
   (SEQ ID NO:4)

5) FNILGGWVA; and/or
   (SEQ ID NO:5)

6) SPVFTDNSSPPAVPQSFQVA
   (SEQ ID NO:6)

and derivatives of them with comparable specificity.

In particular the following derivatives of the HCV epitopes are preferred which contain the HCV epitopes 1) to 5):

7) GENLPYLVAYQATVCARAQA;
   (SEQ ID NO:7)

8) EVVTSTWVLVGGVLAALAA;
   (SEQ ID NO:8)

9) FISGIQYLAGLSTLPGNPAIA;
   (SEQ ID NO:9)

10) PGNPAIASLMAFTAAVTSP; and/or
    (SEQ ID NO:10)

11) SQTLLFNILGGWVAAQLAA
    (SEQ ID NO:11)

and derivatives of them with comparable specificity.

A further solution of the object are the following HCV epitopes specific to $CD4^+$ T-lymphocytes containing the sequence:

```
12)    TSVRLRAYLNTPGLPVCQDH;
       (SEQ ID NO:12)
13)    STEDLVNLLPAILSPGALVV;
       (SEQ ID NO:13)
14)    KLVALGINAVAYYRGLDVSVIPTSGDVVV;
       (SEQ ID NO:14)
15)    SGKPAIIPDREVLYREFDEM;
       (SEQ ID NO:15)
16)    LGIGTVLDQAETAGA;
       (SEQ ID NO:16)
17)    ETAGARLVVLATATP;
       (SEQ ID NO:17)
18)    CVTQTVDFSLDPTFT;
       (SEQ ID NO:18)
19)    RPSGMFDSSVLCECY;
       (SEQ ID NO:19)
20)    VFPDLGVRVVCEKMAL; and/or
       (SEQ ID NO:20)
21)    KLGVPPLRVWRHRAR
       (SEQ ID NO:21)
``` and their derivatives with comparable specificity.

A further solution is a vaccine which contains at least one of the epitopes 1) to 21) according to the invention. Preferably, the vaccine contains the epitope with the position aa1773–1783, that is 3) QYLAGLSTLPG (SEQ ID NO:3).

The vaccine may preferably contain a mixture of the epitopes 1) to 21) according to the invention. However, other HCV epitopes may also be present.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 shows the epitope mapping of the epitope at the position aa1765–1784;

FIG. 2 shows the mapping of the epitope at the position aa1773–1783 using N or C-terminal truncated peptides;

FIG. 3 shows the epitope mapping of the epitope at the position aa1785–1804;

FIG. 4 shows the mapping of the epitope at the position aa1787–1795 using N or C-terminal truncated peptides;

FIG. 5 shows the epitope mapping of the epitope at the position aa1655–1674;

FIG. 6 shows the mapping of the epitope at the position aa1585–1594 using N or C-terminal truncated peptides;

FIG. 7 shows the epitope mapping of the epitope at the position aa1535–1554 with 20 mer peptides;

FIG. 8 shows the epitope mapping of the epitope at the position aa1875–1894 with 20 mer peptides;

FIG. 9 shows the mapping of the epitope at the position aa1689–1708 using N or C-terminal truncated peptides.

DETAILED DESCRIPTION OF THE INVENTION

The epitopes according to the invention are specifically recognised by $CD4^+$ T-lymphocytes which are formed by a self-limiting HCV infection in the patient.

The position of the epitopes according to the invention on the HCV protein is respectively for 1) aa1585–1594, 2) aa1655–1675, 3) aa1773–1783, 4) aa1787–1795, 5) aa1809–1827 and 6) aa1207–1226, 7) aa1580–1599, 8) aa1654–1673, 9) aa1768-1788, 10) aa1782–1800, 11) aa1804–1822, 12) aa1535–1554, 13) aa1875–1894, 14) aa1406-1434, 15) aa1689–1708, 16) aa1327–1341, 17) 1337–1352, 18) aa1457–1472, 19) aa1507-1522, 20) aa2581–2595 and 21) aa2911–2930 whereby the stated positions relate for example to the publications CHOO, Q. -L. et al. PNAS 1991.

The epitopes according to the invention, containing the sequences 1) to 21) quoted above, are preferably the sequences 1) to 21) themselves. In this embodiment of the invention the epitopes according to the invention are selected from the group consisting of

```
1)     YLVAYQATVC,
       (SEQ ID NO:1)
2)     VVTSTWVLVGGVLAALAAYCL,
       (SEQ ID NO:2)
3)     QYLAGLSTLPG,
       (SEQ ID NO:3)
4)     IASLMAFTA,
       (SEQ ID NO:4)
5)     FNILGGWVA,
       (SEQ ID NO:5)
6)     SPVFTDNSSPPAVPQSFQVA,
       (SEQ ID NO:6)
7)     GENLPYLVAYQATVCARAQA,
       (SEQ ID NO:7)
8)     EVVTSTWVLVGGVLAALAA,
       (SEQ ID NO:8)
9)     FISGIQYLAGLSTLPGNPAIA,
       (SEQ ID NO:9)
10)    PGNPAIASLMAFTAAVTSP,
       (SEQ ID NO:10)
11)    SQTLLFNILGGWVAAQLAA,
       (SEQ ID NO:11)
12)    TSVRLRAYLNTPGLPVCQDH,
       (SEQ ID NO:12)
13)    STEDLVNLLPAILSPGALVV,
       (SEQ ID NO:13)
14)    KLVALGINAVAYYRGLDVSVIPTSGDVVV,
       (SEQ ID NO:14)
15)    SGKPAIIPDREVLYREFDEM,
       (SEQ ID NO:15)
16)    LGIGTVLDQAETAGA,
       (SEQ ID NO:16)
```

-continued

17) ETAGARLVVLATATP,
(SEQ ID NO:17)

18) CVTQTVDFSLDPTFT,
(SEQ ID NO:18)

19) RPSGMFDSSVLCECY,
(SEQ ID NO:19)

20) VFPDLGVRVVCEKMAL and
(SEQ ID NO:20)

21) KLGVPPLRVWRHRAR.
(SEQ ID NO:21)

Figure 2:
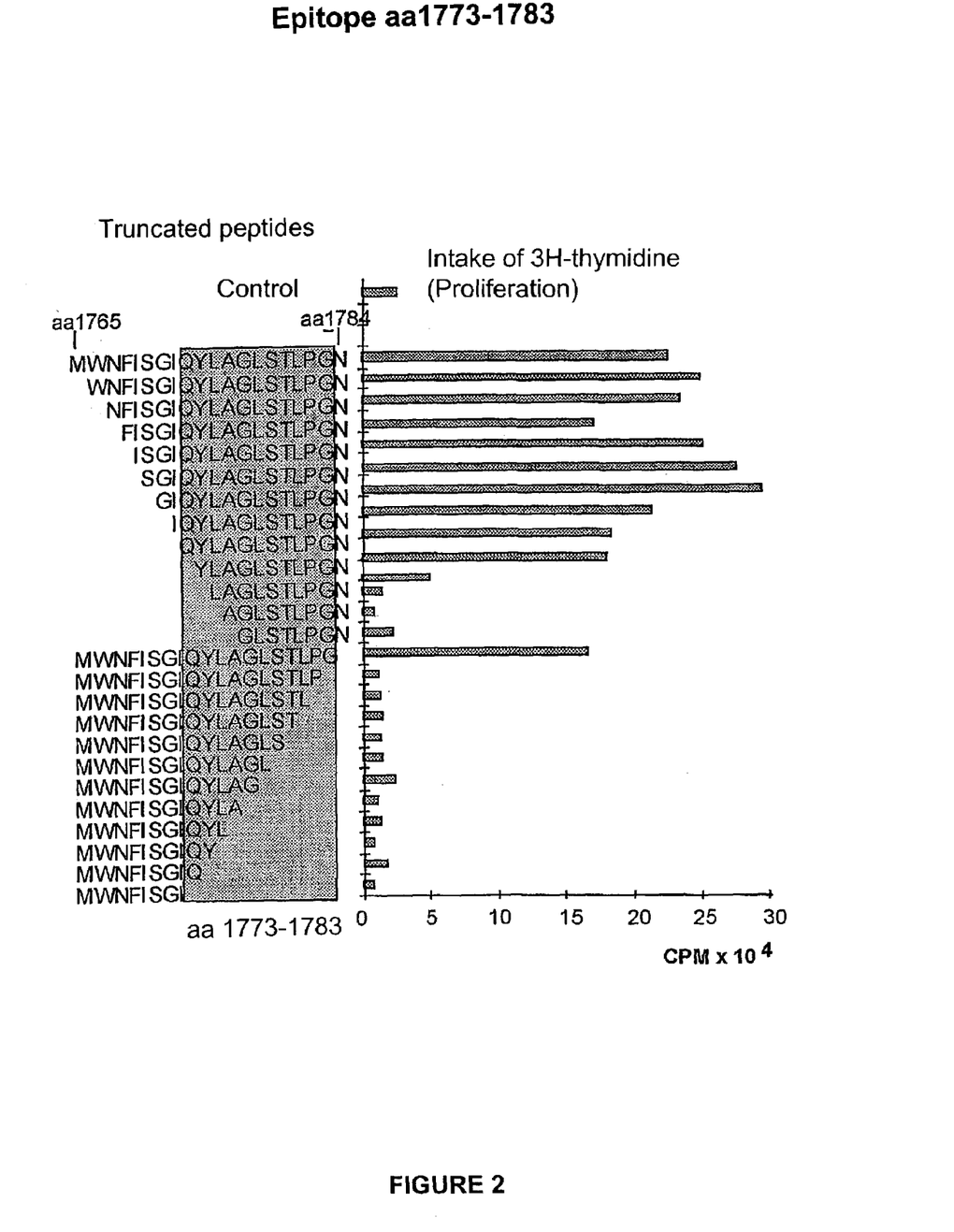
Figure 4:
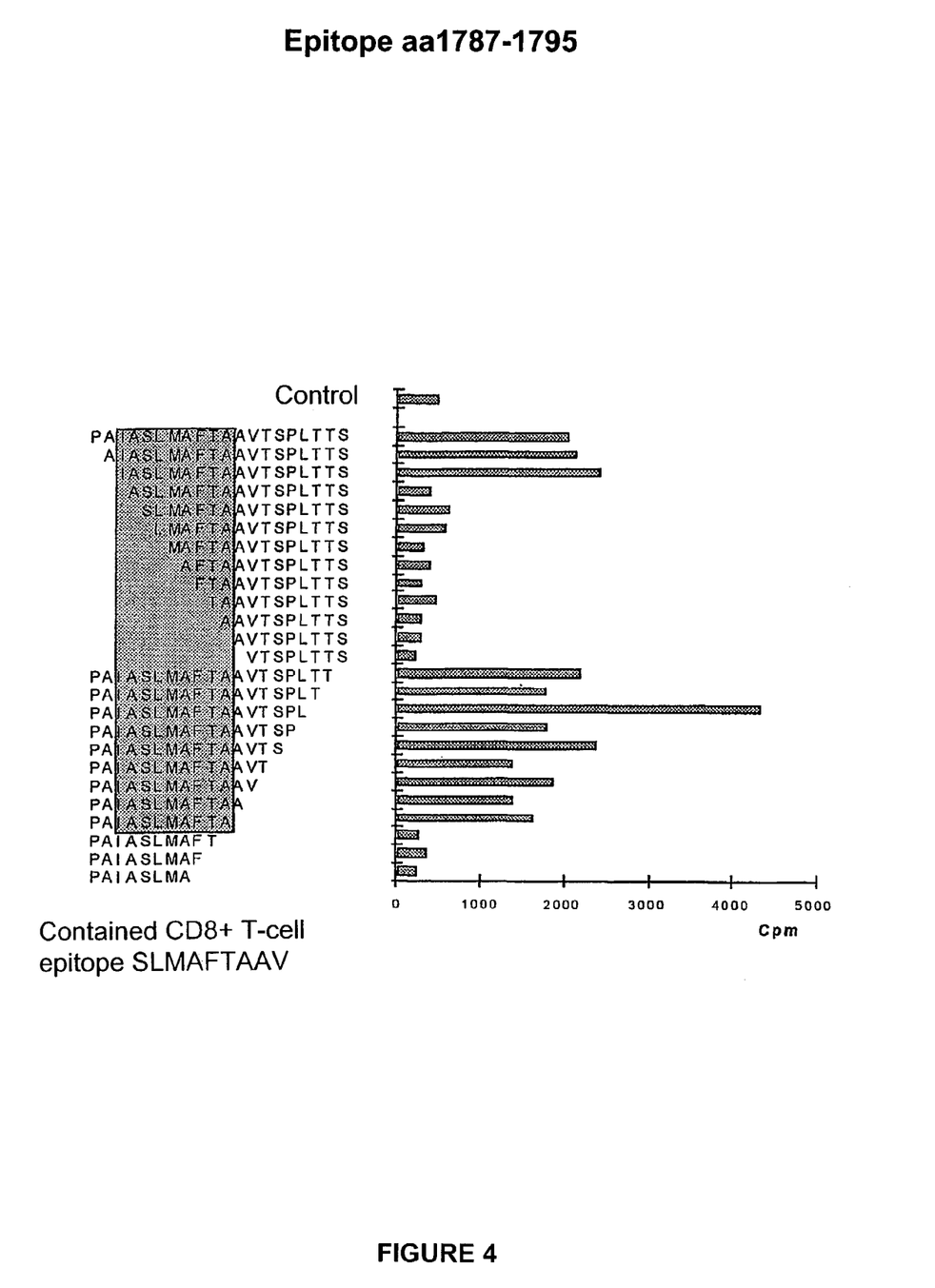
Figure 6:
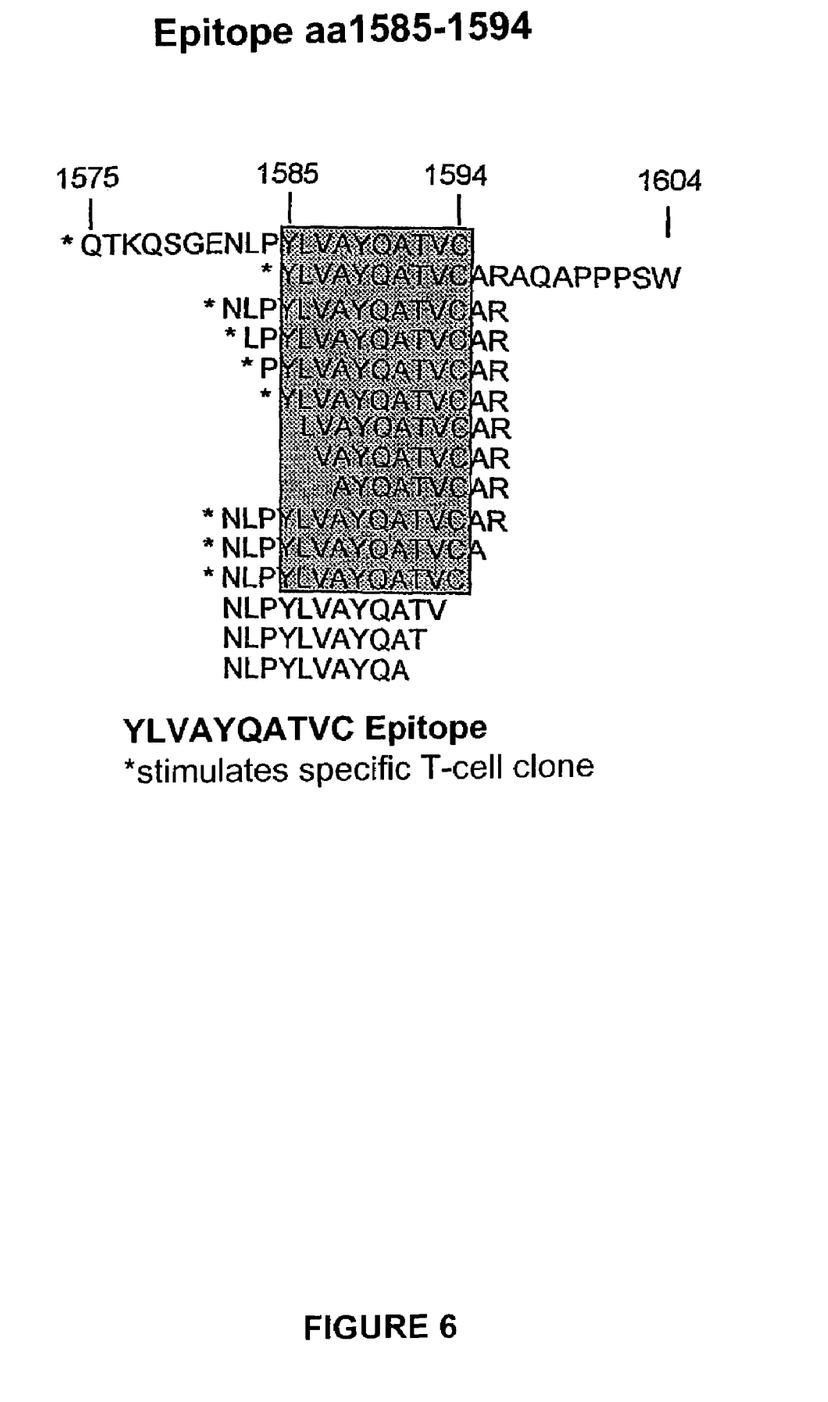
Figure 7:
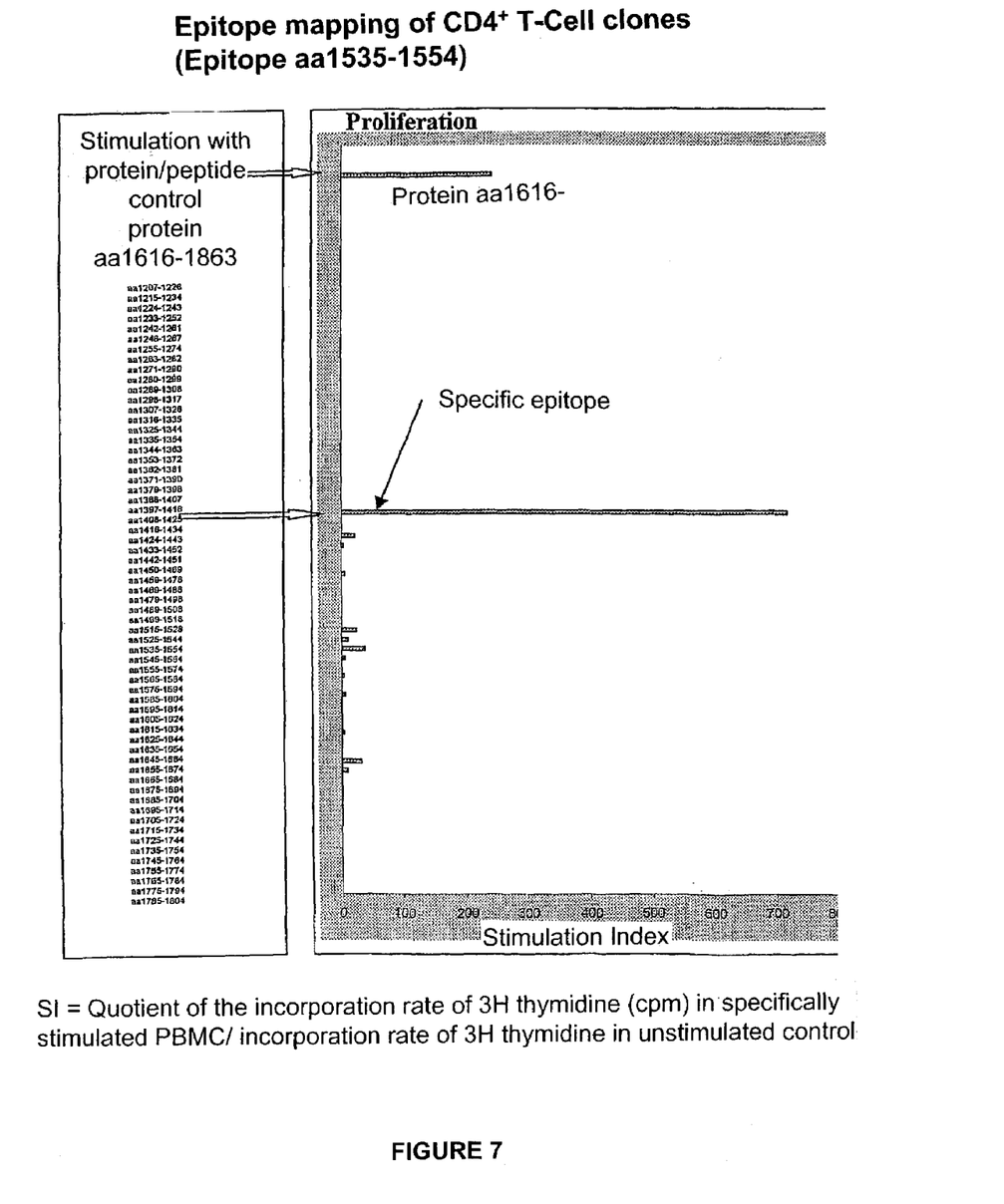
Figure 8:
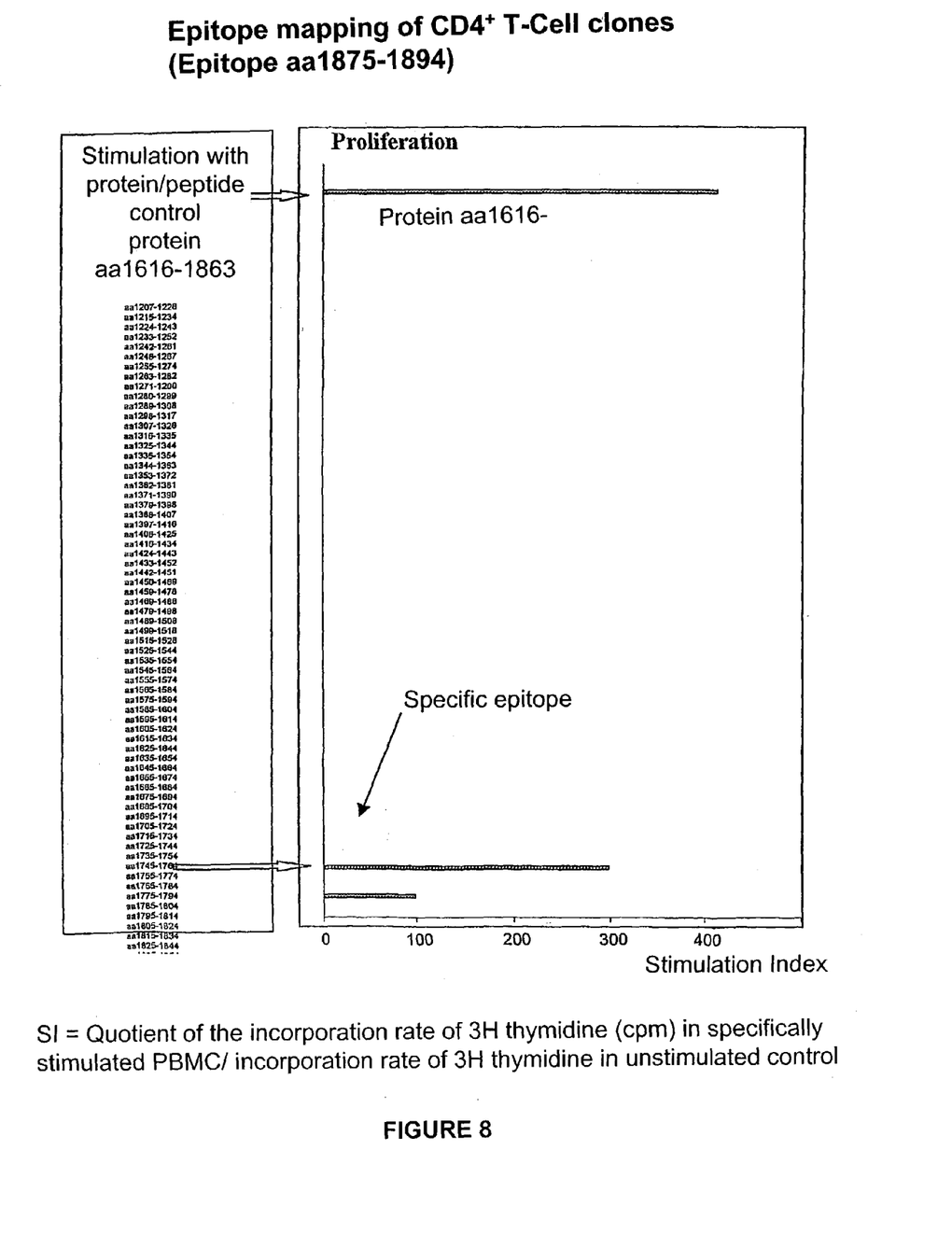
Figure 9:
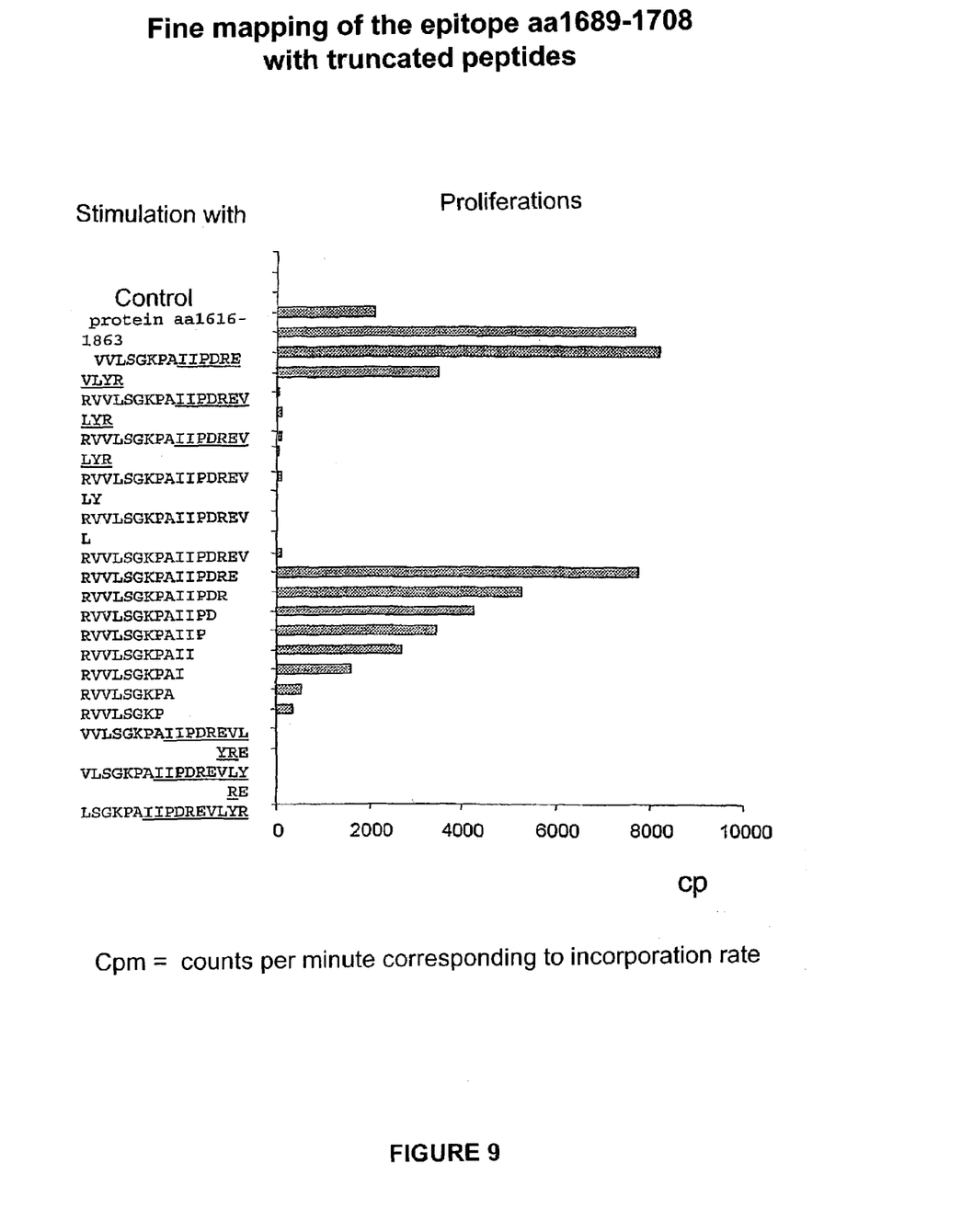

For the identification of these HCV epitopes specific with respect to CD4+ T-lymphocytes, T-cell clones of these virus-specific T-lymphocytes were isolated and cloned out of T-cell lines with the aid of the classical border dilution method with patients with acute Hepatitis C infection who had a self-limiting progression of the illness and with whom a strong HCV-specific T-lymphocyte activity could be simultaneously verified in vitro. This procedure allows the multiplication of a single cell by many powers of ten and enables the characterisation of the antigen specificity with a clonal cell population. An exact characterisation of the respectively recognised epitope using N-terminal and C-terminal truncated peptides, as shown in FIGS. 2, 4 and 6, occurred with the aid of the HCV-specific T-cell clones.

The derivatives of the epitopes 1) to 21) according to the invention with comparable specificity can be found in the same manner as these epitopes by applying the HCV-specific T-cell clones using N and C-terminal truncated peptides or by interchanging single or a number of amino acids in the sequences 1) to 21) and checking the specificity of these changed sequences.

The epitopes according to the invention are highly immunogenous and highly conserved sequences of the HCV which lie in the immediate vicinity to known HCV epitopes specific with regard to CD8+ T-lymphocytes.

As HCV epitopes specific with respect to CD4+ T-lymphocytes, they can, apart from the induction of CD4+ T-lymphocytes, also convey so-called T-cell help for cytotoxic CD8+ T-lymphocytes. These CD8+ T-lymphocytes are activated through the cytokines of stimulated CD4+ T-lymphocytes. In this connection the immediate vicinity of the HCV epitopes found here to known CD8+ epitopes is also particularly important.

The epitopes 1) to 16) were recognised by freshly peripheral mononuclear cells (PBMC) from 18 patients with acute HCV, that is for 1) from 6 patients, for 2) from 4 patients, for 3) from 6 patients, for 4) from 3 patients, for 5) from 4 patients, for 7) from one patient, for 8) from two different clones from one patient, and for 9) and 10) from one patient. The epitopes 11) to 16) were determined with the aid of HCV-specific T-cell clones after liver transplantations from patients with whom a virus elimination had occurred despite immune suppression after the transplantation.

The epitopes according to the invention did not just stimulate the T-lymphocytes of the patients from whom the T-cell clones originated, but also the fresh peripheral mononuclear cells (PBMC) of various patients with acute Hepatitis C and self-limiting course. The HLA (Class I and II), important for the antigen presentation, of these persons with positive reaction to these epitopes was different, so that a certain promiscuity of the peptides (presentation to different HLA receptors) can be assumed. Consequently, in the case of a protective T-cell vaccination, they are excellently suited for the vaccination of healthy people or Hepatitis C patients, each with different HLA characteristics.

The epitopes according to the invention can be employed alone or with one or more adjuvants as medicament, preferably as a vaccine. The vaccine according to the invention contains at least one epitope according to the invention, preferably a mixture of epitopes according to the invention, in particular the epitope at the position aa1773–1783, to which, if required, further epitopes according to the invention or epitopes at other positions can be added.

The adjuvants are preferably selected from the group consisting of fowl pox virus, modified vaccinia virus Ankara, virosomes, TRANSVAX (a tuberculosis epitope vaccine) and other substances which reinforce the immune reaction.

The vaccine according to the invention can be administered orally, parenterally, intramuscularly, intravenously, subcutaneously or intracutaneously.

The epitopes according to the invention are epitopes which can be used as vaccines which stimulate T-cells. A vaccine, containing the epitopes according to the invention, has the advantage compared to vaccination with the complete virus protein, which contains the most varied epitopes for virus-specific T-lymphocytes and which only induces B-lymphocytes and CD4+ T-lymphocytes, in that it selectively induces specific T-lymphocytes, CD4+ and/or CD8+ T-lymphocytes. In addition, antagonistic effects and the risk of iatrogenically produced autoimmune reactions, which can occur with vaccinations with complete proteins, are then avoided. The epitopes according to the invention also have a higher immunogeneity in comparison to the complete virus protein, whereby a better vaccination result is obtained.

The vaccine according to the invention therefore enables the induction of an immune response in healthy people and consequently serves as a prophylactic vaccination. Also with chronically HCV infected people, the vaccine according to the invention can induce an immune response to serve as a therapeutic vaccine.

The coding c-DNA of these epitopes can in a DNA vaccine be employed in a special vaccination method. Here, the coding DNA for the appropriate epitopes is cloned in a vector. This construct is in turn parenterally administered to the individual to be vaccinated (e.g. Immunology and Cell Biology, Volume 75, pages 382 to 388). Various DNA sequences of one of the epitopes according to the invention can be coded according to the degenerated genetic code (refer to Current Protocols, Wiley).

The epitopes according to the invention can also be used in the diagnosis of the course of an HCV infection, in that the ciuantity of CD4+T-lymphocytes which specifically recognize the relevant epitope is monitored in the blood of a patient with a Hepatitis C infection. This can, for example, be carried out with a diagnostic kit which includes one or more of the epitopes of the invention.

EXAMPLE 1

Heparinized blood was taken from patients with a self-limiting course of acute Hepatitis C in the first six months after the start of the illness. The fresh peripheral mononuclear blood cells (PBMC) were isolated by density-gradient centrifugation on Ficoll gradients and suspended in a culture medium (RPMI1640, Gibco). 50 µl of this cell suspension (concentration of $1 \times 10^6$ cells per ml) were transferred to sterile 96-hole culture plates. Ten samples of this cell mixture were each stimulated by the addition of a recombined HCV protein. The final concentration of this protein was 1 µg/ml. The cell culture plates were cultivated over 5 days at 37° C. and 5% $CO_2$. On day 6 the IL-2 was added to the culture. The final concentrations of IL-2 were 15 U/ml and the cells were cultivated for a further three days at 37° C. and 5% $CO_2$. Those holes in the culture plate which appeared to be strongly stimulated during microscopic inspection on Day 10 were collected and distributed in serial dilution stages on another culture plate. A hole was selected microscopically which contained approximately 150 cells. These 150 cells were diluted with medium and distributed over 300 holes, so that statistically half a cell was contained in each hole. Then, IL-2 was added up to a final concentration of 15 U/ml. In addition $3 \times 10^4$ autologous PBMC. irradiated with 3000 Rad, and phythaemagglutinin (PHA) were added as growth factor to each hole. The clones were expanded (multiplied) and then tested for antigen specificity in a proliferation assay with HCV proteins. The antigen specificity was initially determined by stimulation with proteins and then, in the case of a positive result, using peptides (20mer peptides), twenty amino acids in length, as shown in FIG. 1.

Figure 1:
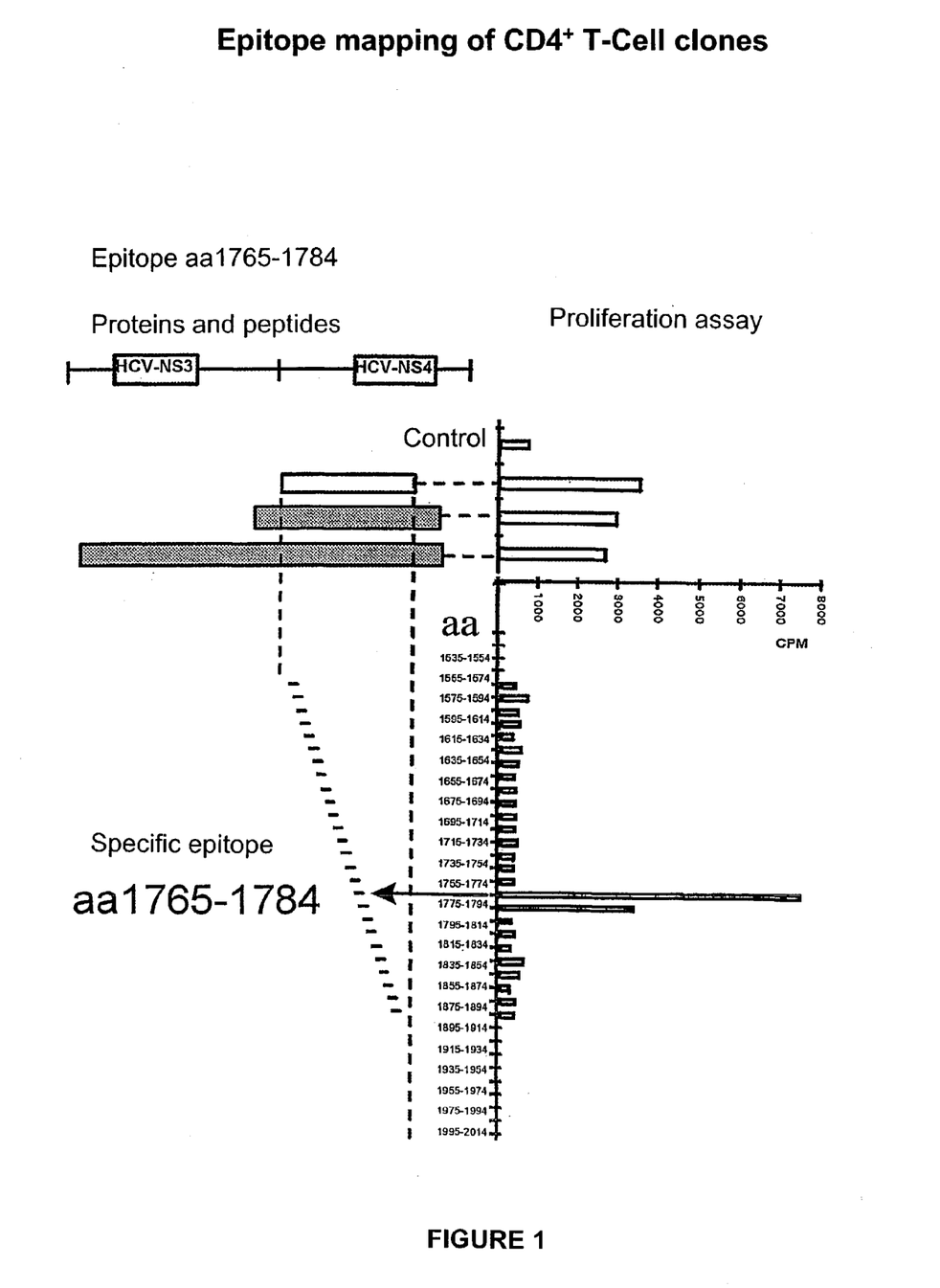

For this, T-cell clones with proteins, as illustrated to the left in FIG. 1, and antigen-presenting cells were stimulated and the stimulation was measured as the incorporation of radioactively labeled 3H, as illustrated to the right in FIG. 1. To further narrow down the specificity detected epitope, stimulation was carried out with 20mer peptides corresponding to the protein secjuence and which each overlap by ten amino acids, and the incorporation of the $^3H$ again measured. In this way the relevant epitope was narrowed down to 20 amino acides.

The epitope, the smallest seciuence which still stimulates within the 20mer peptide, was analysed with truncated peptides. i.e. the original 20mer peptide was shortened in increasing order from N-terminal, as shown in FIG. 2. A similar procedure was used with peptides which were truncated from C-terminal. A proliferation assay showed up to which amino acid the peptide could be shortened without having to accept noticeable stimulation losses.

The epitope OYLAGLSTLPG (SEQ ID NO:3) is obtained as shown in FIG. 2. A high degree of conservation of the epitopes arose through seciuence comparison of the characterized epitopes with seQuences of the known genotypes of whole HCV proteins despite the known high genetic variability of the HCV.

Since peptides are very sensitive to degradation and the antigen-specific recognition of the peptide HLA complex by the T-cell receptor interindividually can be subject to slight variations or can be lost due to the loss of a single amino acid, and as the synthesis length of the peptides can be subject to variation, the epitopes 1 to 5, when used in a vaccine. should carry five amino acids at the N-terminal and C-terminal as protection against degradation and for optimisation of the synthesis and ensuring the antigen presentation, whereby these lengthened epitopes can, for example, be the epitopes 7 to 11.

EXAMPLE 2

Figure 3:
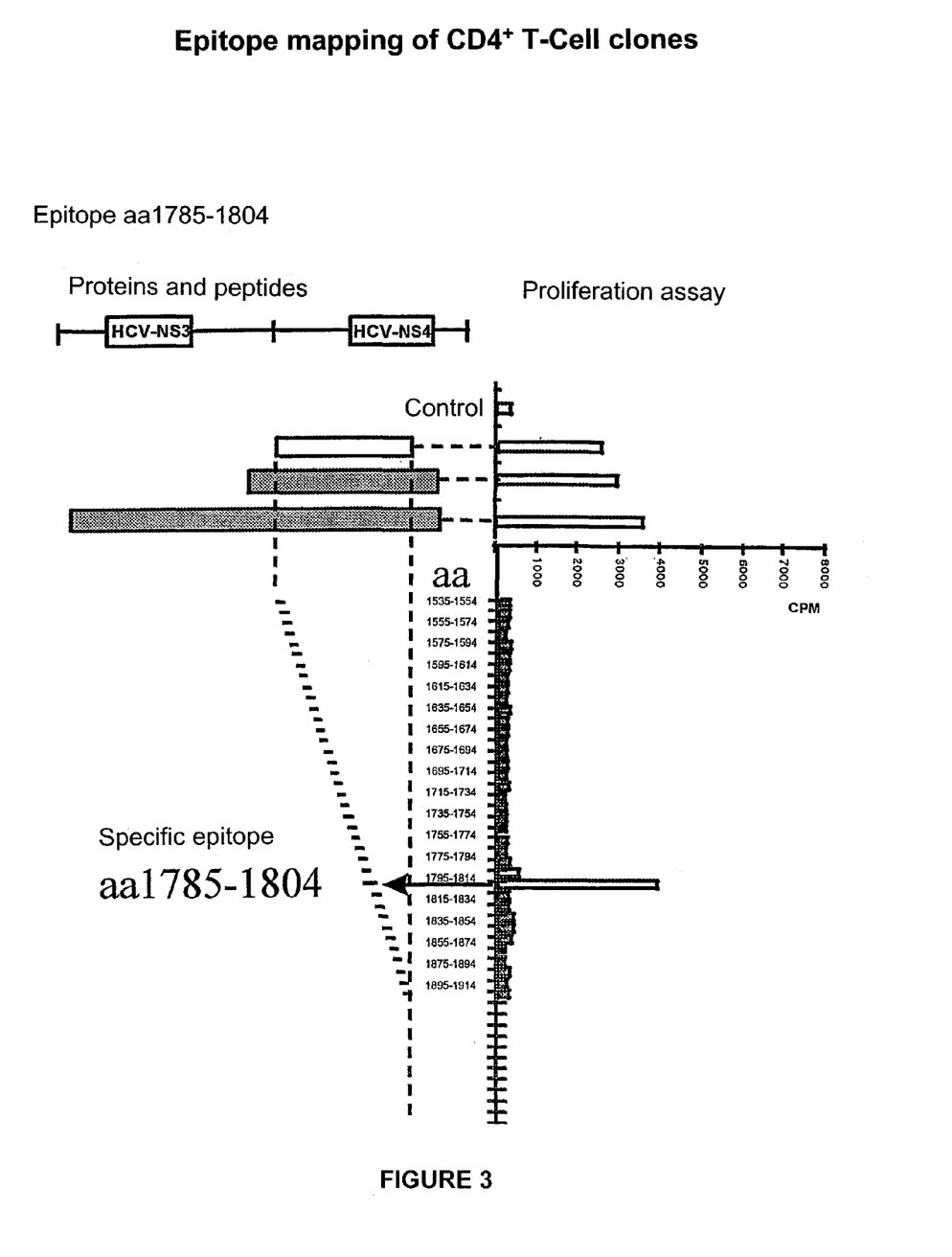

Clones were obtained according to the procedure in Example 1. The antigen specificity of these clones was then determined as shown in FIG. 3. The corresponding epitope with 20 amino acids is obtained. The epitope within this 20mer peptide was then determined as shown in FIG. 4. The epitope IASLMAFTA (SEQ ID NO:4) is obtained.

EXAMPLE 3

Figure 5:
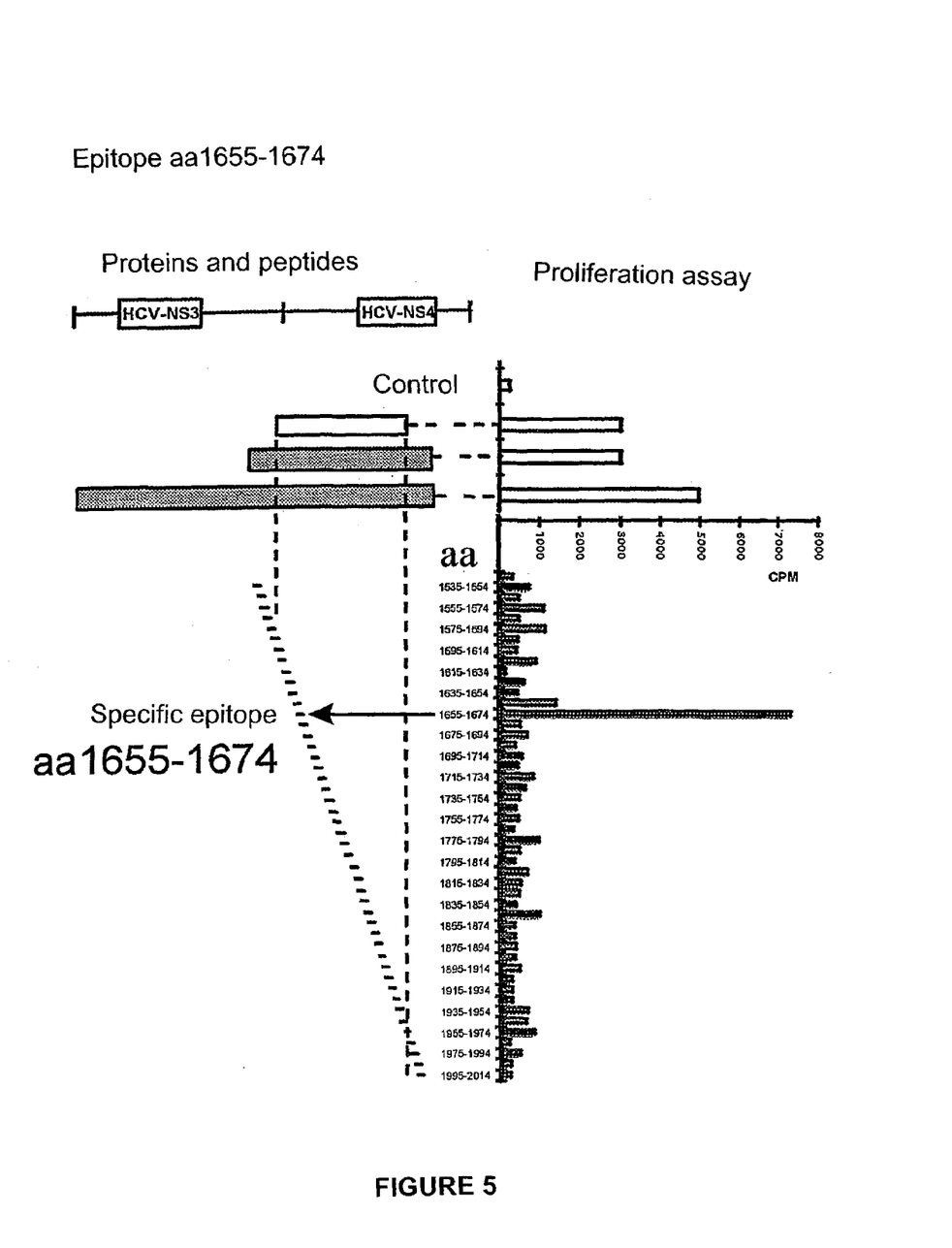

Clones were obtained according to the procedure in Example 1. The antigen specificity of these clones was then determined as shown in FIG. 5. The corresponding epitope with 20 amino acids is obtained, i.e. VVTSTWVLVGGVLAALAAYCL (SEQ ID NO:2), according to Example 1.

I. EXAMPLE 4

Clones were obtained according to the procedure in Example 1. The antigen specificity was also determined as described in Example 1 and the corresponding epitope with 20 amino acids was obtained. As shown in FIG. 6, the epitope was then determined, i.e. YLVAYQATVC (SEQ ID NO:1).

II. EXAMPLE 5

Clones were produced according to the procedure in Example 1 from blood taken routinely from patients after liver transplantations. With patients after liver transplantations the specificity of the T-cell clones was analysed with the aid of ELISPOT assays. Here, a detection antibody which bonded to nitrocellulose, in this case against interferon gamma, was applied to a nitrocellulose-coated microtitter plate.

In the second stage the specific T-cell clones together with antigen-presenting cells and the antigens to be tested were added. After the addition of the specific antigen, the clonal T-lymphocytes secrete interferon gamma, amongst other substances. This cytokine is "intercepted" over 48 hours by the detection antibody. After removal of the cell mixture, a second specific antibody is added which recognises and labels the fixed cytokine antibody complex. The second antibody can then be rendered visible by a dye reaction so that the antigen-specifically secreted cytokines are highlighted as spots which can then be counted under the microscope and which represent a measure of the antigen specificity in relation to the control. Analogous to the proliferation test previously described, epitopes can also be mapped with the ELISPOT assay.

We claim:

1. An isolated polypeptide consisting of the sequence FNILGGWVA (SEQ ID NO: 5).

\* \* \* \* \*

SEQUENCE LISTING

<160> NUMBER OF SEQ ID NOS: 21

<210> SEQ ID NO 1
<211> LENGTH: 10
<212> TYPE: PRT

-continued

<213> ORGANISM: Hepatitis C virus

<400> SEQUENCE: 1

Tyr Leu Val Ala Tyr Gln Ala Thr Val Cys
1               5                   10

<210> SEQ ID NO 2
<211> LENGTH: 21
<212> TYPE: PRT
<213> ORGANISM: Hepatitis C virus

<400> SEQUENCE: 2

Val Val Thr Ser Thr Trp Val Leu Val Gly Gly Val Leu Ala Ala Leu
1               5                   10                  15

Ala Ala Tyr Cys Leu
            20

<210> SEQ ID NO 3
<211> LENGTH: 11
<212> TYPE: PRT
<213> ORGANISM: Hepatitis C virus

<400> SEQUENCE: 3

Gln Tyr Leu Ala Gly Leu Ser Thr Leu Pro Gly
1               5                   10

<210> SEQ ID NO 4
<211> LENGTH: 9
<212> TYPE: PRT
<213> ORGANISM: Hepatitis C virus

<400> SEQUENCE: 4

Ile Ala Ser Leu Met Ala Phe Thr Ala
1               5

<210> SEQ ID NO 5
<211> LENGTH: 9
<212> TYPE: PRT
<213> ORGANISM: Hepatitis C virus

<400> SEQUENCE: 5

Phe Asn Ile Leu Gly Gly Trp Val Ala
1               5

<210> SEQ ID NO 6
<211> LENGTH: 20
<212> TYPE: PRT
<213> ORGANISM: Hepatitis C virus

<400> SEQUENCE: 6

Ser Pro Val Phe Thr Asp Asn Ser Ser Pro Pro Ala Val Pro Gln Ser
1               5                   10                  15

Phe Gln Val Ala
            20

<210> SEQ ID NO 7
<211> LENGTH: 20
<212> TYPE: PRT
<213> ORGANISM: Hepatitis C virus

<400> SEQUENCE: 7

Gly Glu Asn Leu Pro Tyr Leu Val Ala Tyr Gln Ala Thr Val Cys Ala
1               5                   10                  15

Arg Ala Gln Ala
            20

<210> SEQ ID NO 8
<211> LENGTH: 19
<212> TYPE: PRT
<213> ORGANISM: Hepatitis C virus

<400> SEQUENCE: 8

Glu Val Val Thr Ser Thr Trp Val Leu Val Gly Gly Val Leu Ala Ala
1               5                   10                  15

Leu Ala Ala

<210> SEQ ID NO 9
<211> LENGTH: 21
<212> TYPE: PRT
<213> ORGANISM: Hepatitis C virus

<400> SEQUENCE: 9

Phe Ile Ser Gly Ile Gln Tyr Leu Ala Gly Leu Ser Thr Leu Pro Gly
1               5                   10                  15

Asn Pro Ala Ile Ala
            20

<210> SEQ ID NO 10
<211> LENGTH: 19
<212> TYPE: PRT
<213> ORGANISM: Hepatitis C virus

<400> SEQUENCE: 10

Pro Gly Asn Pro Ala Ile Ala Ser Leu Met Ala Phe Thr Ala Ala Val
1               5                   10                  15

Thr Ser Pro

<210> SEQ ID NO 11
<211> LENGTH: 19
<212> TYPE: PRT
<213> ORGANISM: Hepatitis C virus

<400> SEQUENCE: 11

Ser Gln Thr Leu Leu Phe Asn Ile Leu Gly Gly Trp Val Ala Ala Gln
1               5                   10                  15

Leu Ala Ala

<210> SEQ ID NO 12
<211> LENGTH: 20
<212> TYPE: PRT
<213> ORGANISM: Hepatitis C virus

<400> SEQUENCE: 12

Thr Ser Val Arg Leu Arg Ala Tyr Leu Asn Thr Pro Gly Leu Pro Val
1               5                   10                  15

Cys Gln Asp His
            20

<210> SEQ ID NO 13
<211> LENGTH: 20
<212> TYPE: PRT
<213> ORGANISM: Hepatitis C virus

<400> SEQUENCE: 13

Ser Thr Glu Asp Leu Val Asn Leu Leu Pro Ala Ile Leu Ser Pro Gly

-continued

```
                1               5                  10                 15
Ala Leu Val Val
            20

<210> SEQ ID NO 14
<211> LENGTH: 29
<212> TYPE: PRT
<213> ORGANISM: Hepatitis C virus

<400> SEQUENCE: 14

Lys Leu Val Ala Leu Gly Ile Asn Ala Val Ala Tyr Tyr Arg Gly Leu
1               5                   10                  15

Asp Val Ser Val Ile Pro Thr Ser Gly Asp Val Val Val
            20                  25

<210> SEQ ID NO 15
<211> LENGTH: 20
<212> TYPE: PRT
<213> ORGANISM: Hepatitis C virus

<400> SEQUENCE: 15

Ser Gly Lys Pro Ala Ile Ile Pro Asp Arg Glu Val Leu Tyr Arg Glu
1               5                   10                  15

Phe Asp Glu Met
            20

<210> SEQ ID NO 16
<211> LENGTH: 15
<212> TYPE: PRT
<213> ORGANISM: Hepatitis C virus

<400> SEQUENCE: 16

Leu Gly Ile Gly Thr Val Leu Asp Gln Ala Glu Thr Ala Gly Ala
1               5                   10                  15

<210> SEQ ID NO 17
<211> LENGTH: 15
<212> TYPE: PRT
<213> ORGANISM: Hepatitis C virus

<400> SEQUENCE: 17

Glu Thr Ala Gly Ala Arg Leu Val Val Leu Ala Thr Ala Thr Pro
1               5                   10                  15

<210> SEQ ID NO 18
<211> LENGTH: 15
<212> TYPE: PRT
<213> ORGANISM: Hepatitis C virus

<400> SEQUENCE: 18

Cys Val Thr Gln Thr Val Asp Phe Ser Leu Asp Pro Thr Phe Thr
1               5                   10                  15

<210> SEQ ID NO 19
<211> LENGTH: 15
<212> TYPE: PRT
<213> ORGANISM: Hepatitis C virus

<400> SEQUENCE: 19

Arg Pro Ser Gly Met Phe Asp Ser Ser Val Leu Cys Glu Cys Tyr
1               5                   10                  15

<210> SEQ ID NO 20
```

```
-continued

<211> LENGTH: 16
<212> TYPE: PRT
<213> ORGANISM: Hepatitis C virus

<400> SEQUENCE: 20

Val Phe Pro Asp Leu Gly Val Arg Val Val Cys Glu Lys Met Ala Leu
1               5                   10                  15

<210> SEQ ID NO 21
<211> LENGTH: 15
<212> TYPE: PRT
<213> ORGANISM: Hepatitis C virus

<400> SEQUENCE: 21

Lys Leu Gly Val Pro Pro Leu Arg Val Trp Arg His Arg Ala Arg
1               5                   10                  15
```